United States Patent [19]

Kanemaru et al.

[11] Patent Number: 5,698,232

[45] Date of Patent: Dec. 16, 1997

[54] PHARMACEUTICAL COMPOSITION FOR TREATMENT OF SUDDEN DEAFNESS

[75] Inventors: Shinichi Kanemaru, Osaka; Hideyuki Fukushima, Otsu, both of Japan

[73] Assignees: Sumitomo Pharmaceuticals Company, Ltd., Osaka, Japan; Hoffmann-La Roche Inc., N.J.; Takeda Chemical Industries, Ltd., Osaka, Japan

[21] Appl. No.: 745,867

[22] Filed: Nov. 8, 1996

Related U.S. Application Data

[63] Continuation of Ser. No. 296,426, Aug. 26, 1994, abandoned.

[30] Foreign Application Priority Data

Jan. 27, 1994 [JP] Japan ................... 6-007803

[51] Int. Cl.⁶ ........................ A61K 38/19; A61K 31/19
[52] U.S. Cl. ................... 424/85.4; 514/2; 514/21; 514/46; 514/52; 514/59; 514/557
[58] Field of Search ................... 424/85.4; 514/2, 514/21, 59, 46, 52, 557

[56] References Cited

U.S. PATENT DOCUMENTS

5,200,177  4/1993  Leung ................... 424/85.5

OTHER PUBLICATIONS

*Rote Liste* (1991).
*Münch. Med. Wschr.*, vol. 124, No. 42 (1982).
*Jibi Rinsho*, vol. 75, No. 3, pp. 769–778 (1982).
*Am. J. Otol.*, vol. 10, No. 3, pp. 242–247 (1989).
*Laryngoscope*, vol. 72, No. 8, pp. 1142–1157 (1962).
*Arch. Otorhinolaryngol*, vol. 243, pp. 1–15 (1986).
*Jibi*, vol. 28, pp. 878–884 (1982).
*Jibi Rinsho*, vol. 81, No. 4, pp. 515–524 (1988).
*Virus Research*, vol. 15, pp. 1–26 (1990).
*Jikou*, vol. 57, No. 8, pp. 621–628 (1985).

*Primary Examiner*—Gollamudi S. Kishore
*Attorney, Agent, or Firm*—Sughrue, Mion, Zinn, Macpeak & Seas, PLLC

[57] ABSTRACT

An interferon is administered singly or in combination with other pharmacological agents to patients with idiopathic sudden sensorineural hearing loss, whereby the patients are remarkably improved.

4 Claims, 3 Drawing Sheets

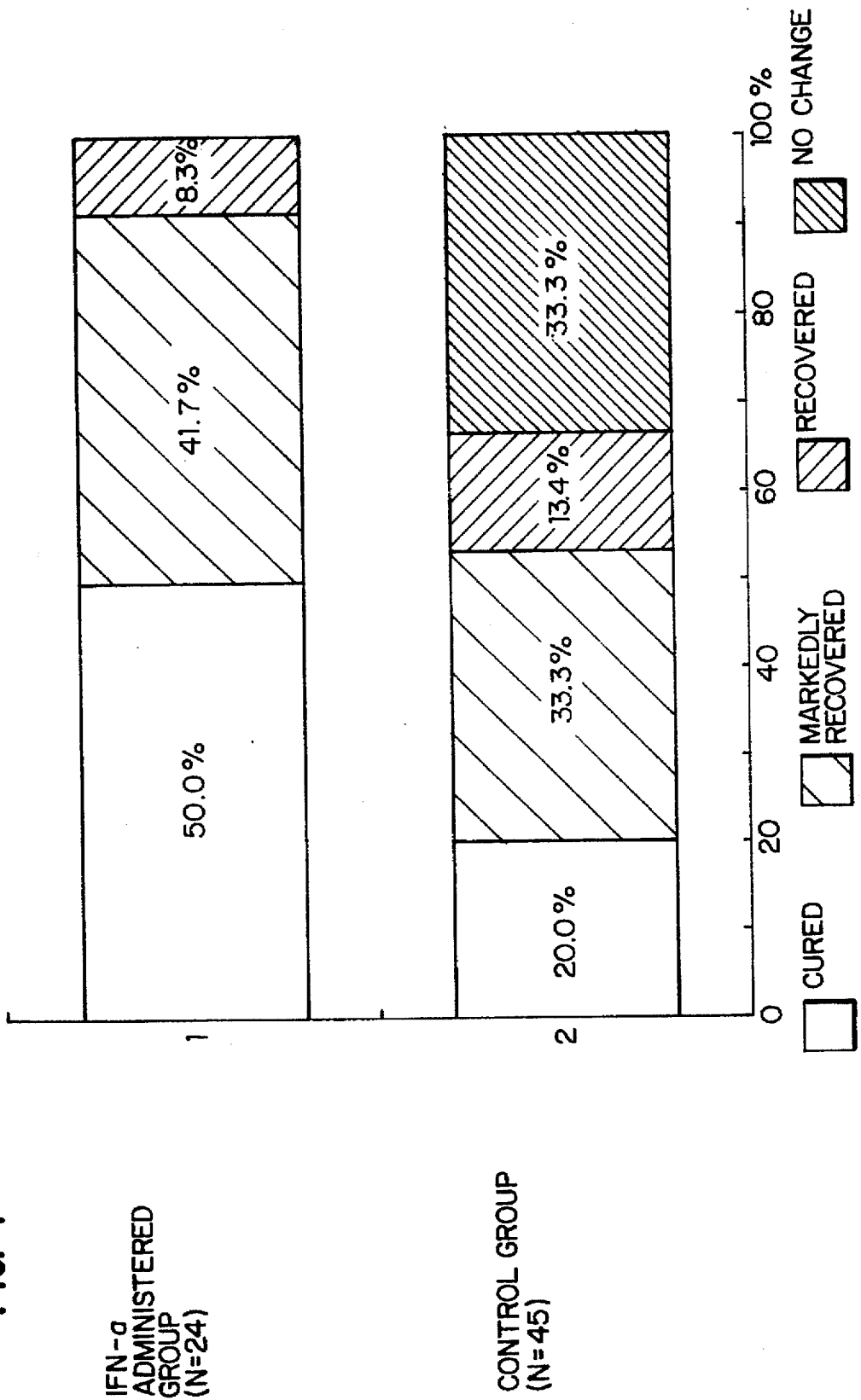

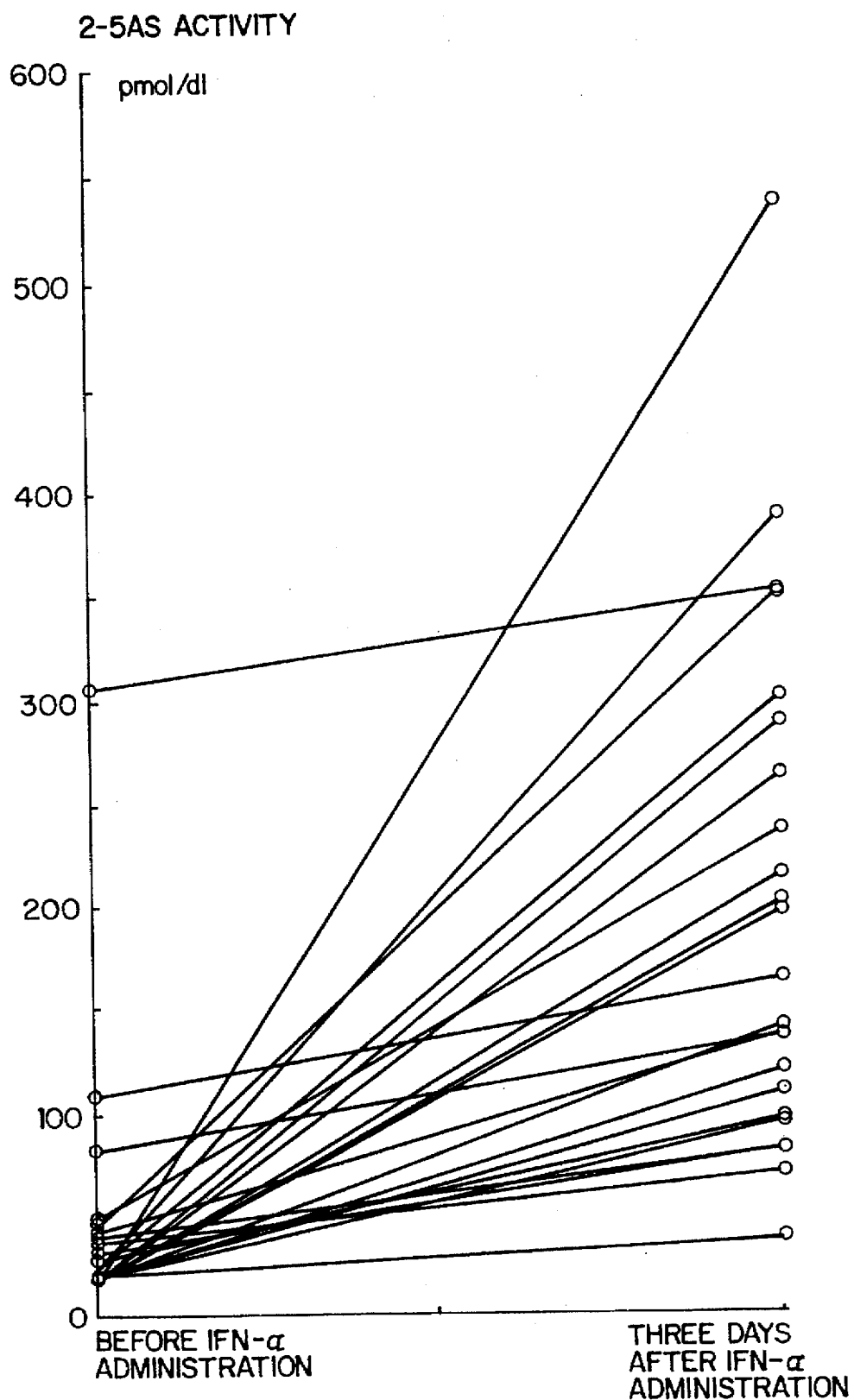

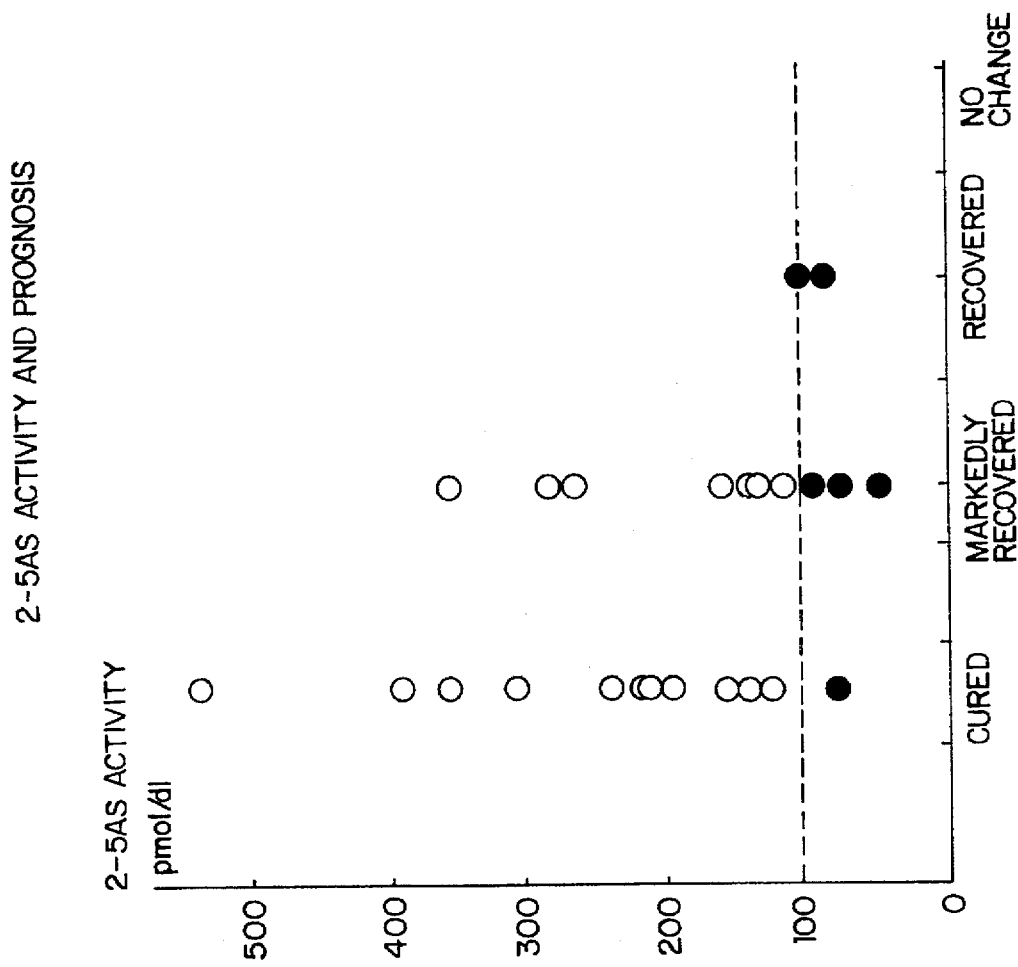

PHARMACEUTICAL COMPOSITION FOR TREATMENT OF SUDDEN DEAFNESS

This is a Continuation of application No. 08/296,426, filed Aug. 26, 1994, abandoned.

BACKGROUND OF THE INVENTION

1. Field of the Invention

The present invention relates to a pharmaceutical composition for the treatment of idiopathic sudden sensorineural hearing loss in human patients.

2. Related Art Statement

Among inner ear deafnesses which have an abrupt onset, deafness with unknown etiology is called idiopathic sudden sensorineural hearing loss (abbreviated ISSHL hereunder). Reference No. 1 (References referred to in the present specification are listed hereinafter), for example, describes: "The Research and Study Group of the Ministry of Health & Welfare: 1973—Idiopathic Sudden Sensorineural Hearing Loss in Special Diseases", as one criteria for diagnosis, calls for "where the time of the initial onset of the symptoms can be clearly determined" and removes from the criteria, "those where etiology can be clearly known". In other words, ISSHL is a syndrome having acute deafness to sound as the main symptom, of which causes are unknown; the onset mechanism and pathema are still under hypotheses. The major proposed hypothetical etiologies are circulation disorder in auris interna, viral infection and labyrinthine window breaks. Those etiologies are merely hypothetical, owing to the impossibility of experimental models of the ISSHL, scarcity of autopsies and those available being obsolete". (see Reference No. 1).

Currently, ISSHL patients are treated with a steroids, cardiovascular agents and vitamins in combination therewith for the purpose of improving blood circulation. Because etiology and pathema of the disease are still unknown, such treatment has not resulted in decisive improvements (see Reference Nos. 1, 2 and 3). Particularly, the treatment for the severe type of ISSHL has not reached any satisfactory results, even where the treatment has been undertaken at an early stage of the disease. Thus, the recovery of practical audio abilities could not be currently obtained.

In 1962, Schuknecht et al. proposed viral infection as the etiology for ISSHL based on his pathological findings in the temporal bones (see Reference Nos. 4 and 5). After that, many reports support the viral infection hypotheses based on enhanced viral antibody plasma levels from patients with ISSHL (see Reference Nos. 6 and 7). However, in view of the treatment of ISSHL, there has been almost no prior art wherein antiviral agents are used for the treatment of ISSHL. Even though such prior art has been proposed, they have not resulted in satisfactory improvements. For example, according to Reference No. 7, researchers considered that the rate of cure may be enhanced by using antiviral agents in the treatment for ISSHL, and thus, carried out the combined use of an antiviral agent, Acyclovir, with conventional treatment. However, there were observed no significant differences between the groups of steroid and Acyclovir, Acyclovir alone and steroid alone. Under such circumstances, it may be considered that the positive treatment of ISSHL in consideration of viral infection has not been hitherto undertaken.

Incidentally, an interferon (abbreviated IFN hereunder) is known as a biologically active protein showing an antiviral activity. IFN is a substance produced owing to various causes such as viral infection, and is one of cytokines having biological activities such as antiviral, anti-tumor, immune regulatory activities, and the like. Although the total feature of the antiviral activities of IFN have not yet been known, it is known to act on the cells but not directly against virus and activate 2',5'-oligoadenylate synthetase (abbreviated 2-5 AS hereunder), resulting in the destruction of viral mRNA to exhibit an antiviral activity (see Reference Nos. 10, 11 and 12). However, it is not known whether IFN shows in vivo antiviral activities against all viral infections.

Applications of such IFN in the treatment for ISSHL has not been reported so far. There is, however, one example of applying human IFN-α to patients with Varicella-Zoster Virus infection, which is not ISSHL but one of the symptoms of deafness (see Reference No. 13). As a result of the treatment, symptoms (e.g., pharyngalgia, pain in the ear (otalgia dextri), pyrexia, disturbance of consciousness, etc.) other than deafness are improved, but deafness failed to be improved, remaining unchanged for two months after the onset of the disease.

SUMMARY OF THE INVENTION

An object of the present invention is to provide a novel pharmaceutical composition for the treatment of ISSHL. That is, the problem to be solved by the invention resides in providing a pharmaceutical composition containing IFN for the treatment of ISSHL which shows superior effects and has not been hitherto available.

When IFN was administered to patients with ISSHL alone or in combination with pharmaceutical agents conventionally used for patients with ISSHL, some improving effects were recognized in all patients, and many patients were markedly improved; the present invention has been thus achieved.

Accordingly, in a first aspect, the present invention relates to a pharmaceutical composition for the treatment of ISSHL comprising IFN as an effective ingredient.

In a second aspect, the present invention relates to use of an interferon alone or in combination with one or more other pharmaceutical agents in the manufacture of a medicament for the treatment of ISSHL.

In a third aspect, the present invention relates to use of an interferon alone or in combination with one or more other pharmaceutical agents to treat ISSHL.

In a fourth aspect, the present invention relates to a method for the treatment of ISSHL, which comprises administering to a human body an interferon alone in an effective amount or in combination with one or more other pharmaceutical agents.

BRIEF DESCRIPTION OF THE DRAWINGS

FIG. 1 shows therapeutic results in the group after administering with IFN-α and in control group.

FIG. 2 shows changes in 2-5 AS activity before IFN-α administration and day 3 after IFN-α administration. 2-5AS has an antiviral activity at 100 pmol/dl or more.

FIG. 3 shows the relationship between 2–5 AS activity levels day 3 after IFN-α administration and prognosis, wherein ○ and ● denote more than 100 pmol/dl and less than 100 pmol/dl, of 2-5 AS activity, respectively.

DETAILED DESCRIPTION OF THE INVENTION

IFN to be contained in the present composition may be those derived from any natural material (e.g., leukocytes, fibroblasts, lymphocytes) or material derived therefrom (e.g., cell lines), or those prepared with recombinant DNA technology.

Details of the cloning of IFN cDNA and the direct expression thereof, especially in E. coli, have been the subject of many publications. Thus, for example, the preparation of recombinant IFNs is known, for example, from Nature 295 (1982), 503–508 (Gray et al.), Nature 284 (1980), 316–320, Nature 290 (1981), 20–26 (Goeddel et al.), Nucleic Acids Res. 8 (1980), 4057–4074i, as well as from European Patent No. 174143.

There are many types of IFN such as α-, β- and γ-IFNs; and further their subtypes including but not limited to IFN-αI, IFN-α2 (such as IFN-α2A, IFN-α2B, IFN-α2C), IFN-αII (also designated IFN-$α_{II}$ or ω-IFN); natural and artificial allelic variants; and IFN molecules containing inversions, deletions, insertions and modifications (such as pegylated IFNs) as well as any hybrid or consensus IFN molecules obtainable from the aforementioned molecules, all of which may be effectively used in the present composition.

The pharmaceutical composition according to the present invention may comprise IFN singly or in combination with one or more of other pharmaceutical agents. Alternatively, the composition comprising IFN singly may be used in combination with a pharmaceutical composition comprising one or more of other pharmaceutical agents. Other pharmaceutical agents noted above include those conventionally used for the treatment of ISSHL, such as steroids, e.g., betamethasone, prednisolone, etc.; cardiovascular agents or vasodilators, e.g., ATP, kallikrein, prostaglandins, low molecular weight dextran, etc.; and vitamins, e.g., vitamin $B_2$, etc.

Thus, the pharmaceutical composition according to the present invention is also expected to accelerate the treatment effect of idiopathic sudden sensorineural hearing loss by other pharmaceutical agents.

The pharmaceutical composition may be in the form of a set comprising IFN and one or more of other pharmaceutical agents.

The composition according to the present invention may further contain pharmaceutically acceptable carriers which are suitable for the desired administration route in the therapy of ISSHL. For example, carriers for injection fluid may include sterilized aqueous isotonic physiological saline solution, preservatives, buffer, and the like. The composition according to the present invention may be prepared in the form of a sustained release composition.

Daily dosage may be variable in the range of 100 to 20,000,000 units, until effects are noticeable, and a more desirable range of daily dosage should be 500,000 to 10,000,000 units for about 2 weeks.

Intramuscular administration is preferably recommended, and oral, annular, subcutaneous, intravenous, topical, intraventricular and intraperitoneal administrations may also be applied.

The present invention is further illustrated with reference to the examples but is not intended to be restricted thereby in any way.

EXAMPLES (1) Method

IFN-α [IFN ALFA-2A (genetical recombination)] was intramuscularly administered in a dose of 3,000,000 units to patients for consecutive 10 days.

In addition to the treatment with a circulation-improving vasodilator (e.g., low molecular weight dextran and ATP), a vitamin (e.g., vitamin $B_{12}$) and nicotinic acid, steroid taperling therapy (e.g., betamethasone) was simultaneously performed. The details are shown in Table 1.

TABLE 1

| Day | IFN-α (i.m.) | Betamethasone Sodium Phosphate (drip infusion) | Other Medicaments* (drip infusion) |
|---|---|---|---|
| 1–3 | 3,000,000 units | 100 mg | Low molecular weight dextran (300 ml); |
| 4–6 | 3,000,000 units | 50 mg | Isotonic sodium (300 ml); |
| 7–9 | 3,000,000 units | 25 mg | ATP (40 mg × 2); |
| 10 | 3,000,000 units | 0 mg | Vitamin $B_{12}$ (500 μg); and |
| 11–14 | 0 units | 0 mg | Nicotinic acid (20 mg × 2) |

*All of other medicaments were administered everyday for 14 days.

(2) Subject

Among the outpatients with ISSHL who received the treatment from August in 1992 to November in 1993, evaluation was focused particularly on the patients with the severe type of ISSHL which is generally considered to be unsatisfactory in prognosis. That is, the subject was only the patients within one week from the disease onset and having 70 dB or more average auditory capacity at the first examination according to a 5-class method (N=24, age: 20–78 years old, 7 males, 17 females; average auditory capacity at the first examination: 86.6 db as determined according to the 5-class method, 12 for the right ear, 12 for the left ear, average time span for the treatment: 3.4 days). The 5-class method comprises determining the arithmetical average of auditory capacity at 5 frequencies of 250, 500, 1000, 2000 and 4000 Hz.

The details of the subject are summarized in Table 2.

TABLE 2

| | Age (years old) | Sex | Average Auditory Capacity at the First Examination |
|---|---|---|---|
| Group administered with IFN-α (N = 24) | 53.4 +− 13.9 | Male: 7 Female: 17 | 86.6 +− 8.8 dB |
| Control group (N = 45) | 41.9 +− 15.8 | Male: 26 Female: 19 | 85.1 +− 14.9 dB |

In the above treatment, the patients were sufficiently informed of ISSHL as well as the use of IFN-α for the treatment and side-effects accompanied thereby, and thus they gave their consent to the treatment. Three out of 24 patients did not receive steroid taperling therapy, while treated with IFN-α and the circulation-improving vasodilator, since they were diabetics.

For control, there were used therapeutic results obtained with patients within one week after the disease onset and having 70 dB or more average auditory capacity at the first examination according to a 5-class method (N=45, age: 13–89 years old, 26 males, 19 females, average auditory capacity at the first examination: 85.1 dB as determined according to the 5-class method, 20 for the right ear, 25 for the left ear, average time span of the treatment: 3.8 days), among the patients who received steroid taperling therapy from January in 1988 to July in 1992. The therapeutic effect was determined by a 4-stage evaluation according to the criteria of hearing recovery set forth by The Research and Study Group of the Ministry of Health & Welfare:— Idiopathic Sensorineural Hearing Loss. The details of the criteria are shown in Table 3.

TABLE 3

|  | Criteria of Therapeutic Effects |
| --- | --- |
| Cured | 1) In auditory capacity test, 250, 500, 1000, 2000 and 4000 Hz recovered to within 20 dB. |
|  | 2) When auditory capacity at the normal site is considered stable, the capacity at the site of lesion is recovered to the same level. |
| Markedly recovered | When arithmetical average of the above 5 frequencies is improved by 30 dB or better. |
| Recovered | When arithmetical average of the above 5 frequencies is improved by 10–29 dD. |
| Unchanged | When arithmetical average of the above 5 frequencies is changed within +− 9 dB. |

(3) Results

Therapeutic effects are shown in FIG. 1.

In the control group, there is no significant difference from the results hitherto reported in other hospitals (see Reference Nos. 1, 2, 8 and 9). As is clear from comparison between the IFN-α administered group and the control group, 12 out of 24 patients, about one half, were completely cured but none were found to be unchanged. On the other hand, 9 out of 45 patients (20%) were cured but 15 out of 45 patients, which is ⅓ of the total patients, showed no change. These results indicate that there is a significant difference between the IFN-α administered group and the control group. Effective rate obtained from FIG. 1 is as follows:

Effective rate: 100% in the IFN-α group
66.7% in the control group
($X^2$ test: $X^2$=9.97, p<0.0016)

Furthermore, comparison was made with the restricted patients with the more severe type of ISSHL having 90 dB or more average auditory capacity and including at least one scaling out. That is, the restricted patients had auditory capacity of the dB level more than the scaling out recognition dB shown in Table 4 on at least one frequency among the 5 frequencies.

TABLE 4

| Hz | Scaling Out Recognition dB |
| --- | --- |
| 250 | 80 dB or more |
| 500 | 100 dB or more |
| 1,000 | 100 dB or more |
| 2,000 | 100 dB or more |
| 4,000 | 100 dB or more |

The obtained results are shown in Table 5.

As shown in Table 5, 10 out of 24 patients in the IFN-α administered group corresponded to those with the more severe type of ISSHL, in which 3 patients were cured, 6 patients were markedly recovered and one patient was recovered. In the control group, 14 out of 45 patients corresponded to those with the more severe type of ISSHL, none was found to be cured or markedly recovered 4 patients were recovered and 10 patients were unchanged. Effective rate is as follows:

Effective rate: 100% in the IFN-α group
28.5% in the control group
(Fischer's Exact test, 2-tail: p<0.0001)

Prognosis of 3 patients with diabetes who could not receive steroid taperling therapy showed cured, markedly recovered and recovered results, respectively.

No side effect was observed even in the dose of 3,000,000 units of IFN-α.

The results of these therapeutic effects reveal that IFN-α is effective also for the more severe type of ISSHL which were hardly cured by conventional treatments.

TABLE 5

| Therapeutic Effects (90 dB or more in average auditory capacity) | | |
| --- | --- | --- |
|  | IFN-α administered Group | Control Group |
| Cured | OOO |  |
| Markedly recovered | OOOOOO |  |
| Recovered | O | OOOO |
| Unchanged |  | OOOOOOOOOO |

(4) Determination of 2-5 AS activity

As described above, IFN exhibits an activity of inhibiting viral proliferation and 2-5 AS is an index of the antiviral activity (Reference Nos. 10–12). In the group administered with IFN-α, 2-5 AS activity in blood was determined at the first examination and 3 days after IFN-α administration, in order to evaluate any relationship with prognosis. In this test, 2-5 AS activity was determined by measuring the amount of 2-5 A synthesized by 2-5 AS with Radio Immuno Assay (e.g., 2 antibody method). For the measurement, "2-5 A Kit" manufactured by EIKEN KAGAKU Co., Ltd. was employed.

FIG. 2 shows relationship between prognosis and changes in 2-5 AS activity before and after IFN-α administration. It has been reported that 2-5 AS shows an antiviral activity on the level of 100 pmols/dl or more (SRL Co., Ltd., "2'-5' oligo adenylic Acid Synthetase Test Manual Cod 5462). As shown in FIG. 2, it is considered in most cases that there is no antiviral activity at 2-5 AS level below 100 pmol/dl before IFN-α administration. On the other hand, day 3 after IFN-α administration, the 2-5 AS level is more than 100 pmol/dl 5 in most cases. Except for one case which showed to be cured, the 2-5 AS activity was increased in almost all cases (Paired-t test: t=6.14, p<0.0001).

FIG. 3 shows relationship between the 2-5 AS activity level day 3 after IFN-α administration and prognosis. In 91.7% (e.g., 11 out of 12 cases) in the cured cases and in 70.0% (e.g., 7 out of 10 cases) in the markedly recovered cases, the 2-5 AS activity level was found to be increased. However, in the recovered cases, the increase in the 2-5 AS activity level was not noted in any of two cases. These results indicate a close correlation between increased 2-5 AS activity day 3 after IFN-α administration and prognosis (Fisher's Exact test, 2-tail: p=0.054).

As described above, the increase in 2-5 AS activity was noted in 75.0% (e.g., 18 out of 24 cases) 3 days after IFN-α administration. Therefore, it is considered that the increase in 2-5 AS activity would be induced by IFN-α administration to provide antiviral conditions. In addition, the results that prognosis was significantly better in the cases showing a high 2-5 AS activity than in the conventional treatment suggest that virus would be somewhat involved in the etiology of ISSHL.

References:

1. Ohashi, M.: "Clinical analysis on pathogenesis and treatment of idiopathic sensorineural hearing loss", Audiol. Jpn., 30: 124–140, 1987
2. Yanagida, N., Suzuki, Y., Murahashi, K., et al.: "Prognosis and Pathogenesis of Sudden Deafness with Scaling Out", JIBI RINSHO, 75: 769–778, 1982,
3. Mattox, D. E. and Lyles, C. A.: Idiopathic sudden sensorineural hearing loss, Am. J. Otol., 10: 242–247, 1989
4. Schuknecht, H. F., Benitez, J., Beekhuis, J. Igarashi, M., et al.: The pathology of sudden deafness, Laryngoscope, 72: 1142–1157, 1962
5. Schuknecht, H. F. and Donovan, E. D.: The pathology of idiopathic sudden sensorineural hearing loss, Arch. Otorhinolaryngol, (Berlin) 243: 1–15, 1986
6. Motofuji, R., Kurata, T., Nomura, Y., et al.: Serological study of herpes simplex virus in patients with idiopathic sensorineural hearing loss, JIBI, 28: 878–884, 1982
7. Nakanishi, H., Enomoto, M., Samukawa, T.: Drip Infusion Therapy of Antiviral Agent for Sudden Deafness, JIBI RINSHO, 81: 4, 515–524, 1988
8. Omura, M., Yamamoto, E., Hirono, Y., et al.: Therapeutic results of sudden deafness in this department, AUDIOLOGY JAPAN, 32: 329–330, 1989
9. Matsui, K., Nozue, M., Seki, A., et al.: Therapy of sudden deafness by Solu-Medrol, JIBI RINSHO, 84: 1333–1338, 1991
10. Taylor, J. L., Grossberg, S. E.: Recent progress in interferon research, Virus Research, 15: 126, 1990
11. Imanishi, J.: Cytokine therapy—approach from basic pathogenesis, interferon (edited by Takaku, F.), 89–106, Nankodo Publishing Co., Tokyo, 1992
12. Yamazaki, S.: Viral infections and interferon, SAISHIN IGAKU, 29: 623–630, 1974
13. Ono, H., Takenaka, Y. et al.: Intramedullary administration of interferon against labyrinthine disturbance induced by herpes zoster, JIKOU, 57 (8): 621–628, 1985

What is claimed is:

1. A method for the treatment of idiopathic sudden sensorineural hearing loss, which comprises administering to a subject in need of such treatment a pharmaceutically effective amount of an α-interferon.

2. The method of claim 1 wherein the α-interferon is derived from nature or prepared with recombinant DNA technology.

3. The method of claim 1, wherein said α-interferon is administered in combination with a pharmaceutically effective amount of at least one pharmaceutical agent selected from the group consisting of a steroid, ATP, a low molecular weight dextran, vitamin B12, and a nicotinic acid.

4. The method of claim 1, further comprising the step of administering a pharmaceutical composition comprising a pharmaceutically effective amount of at least one pharmaceutical agent selected from the group consisting of a steroid, ATP, a low molecular weight dextran, vitamin B12, and a nicotinic acid.

* * * * *